US009365217B2

(12) United States Patent
Bridgers et al.

(10) Patent No.: US 9,365,217 B2
(45) Date of Patent: Jun. 14, 2016

(54) MOBILE POTHOLE DETECTION SYSTEM AND METHOD

(71) Applicant: Booz-Allen & Hamilton, McLean, VA (US)

(72) Inventors: James Bridgers, Dayton, OH (US); Tony Chiang, Centreville, OH (US)

(73) Assignee: BOOZ ALLEN HAMILTON INC., McLean, VA (US)

( * ) Notice: Subject to any disclaimer, the term of this patent is extended or adjusted under 35 U.S.C. 154(b) by 195 days.

(21) Appl. No.: 13/908,803

(22) Filed: Jun. 3, 2013

(65) Prior Publication Data

US 2014/0355839 A1    Dec. 4, 2014

(51) Int. Cl.
| | |
|---|---|
| *G06K 9/00* | (2006.01) |
| *B60W 40/06* | (2012.01) |
| *G06T 7/00* | (2006.01) |
| *G01N 21/00* | (2006.01) |

(52) U.S. Cl.
CPC .............. *B60W 40/06* (2013.01); *G06T 7/0004* (2013.01); *G01N 21/00* (2013.01); *G01N 2223/614* (2013.01); *G06T 2207/30132* (2013.01); *G06T 2207/30184* (2013.01)

(58) Field of Classification Search
CPC .. G01N 21/00; G01N 2223/614; B60W 40/06
See application file for complete search history.

(56) References Cited

U.S. PATENT DOCUMENTS

| | | | | |
|---|---|---|---|---|
| 5,817,936 A | * | 10/1998 | Schricker | ........... B60G 17/0165 73/105 |
| 6,615,648 B1 | | 9/2003 | Ferguson et al. | |
| 6,952,487 B2 | * | 10/2005 | Patton | .................... G01C 11/02 252/301.19 |
| 8,275,522 B1 | * | 9/2012 | Groeneweg | ............ G06Q 10/06 701/50 |
| 8,370,030 B1 | | 2/2013 | Gurin | |
| 8,930,074 B1 | * | 1/2015 | Lin | ..................... B60G 17/0165 340/438 |
| 2005/0065666 A1 | * | 3/2005 | Miyashita | ............... B60C 19/00 701/1 |
| 2009/0076698 A1 | * | 3/2009 | Yokoyama | ................ B60T 7/22 701/70 |
| 2009/0259686 A1 | * | 10/2009 | Figueroa | ........... G06F 17/30038 |
| 2012/0158820 A1 | * | 6/2012 | Bai | ......................... G07C 5/008 709/202 |
| 2014/0310702 A1 | * | 10/2014 | Ricci | ..................... H04W 48/04 717/173 |
| 2015/0178572 A1 | * | 6/2015 | Omer | ................. G06K 9/00798 382/108 |

OTHER PUBLICATIONS

Christian et al (Pothole detection in asphalt pavement images, Advanced engineering informatics 25 (2011), pp. 507-515).*
Colleen Collins, et al., "Transmap 200." *Ohio GIS Conference*, Columbus, Ohio, Sep. 15-17, 2010.
Jakob Eriksson, et al., The Pothole Patrol Using a Mobile Sensor Network for Road Surface Monitoring. *MIT Computer Science and Artificial Intelligence Laboratory*. Breckenridge, Colorado, 2008.

(Continued)

*Primary Examiner* — Amara Abdi
(74) *Attorney, Agent, or Firm* — Buchanan Ingersoll & Rooney PC

(57) ABSTRACT

An exemplary apparatus and associated method are disclosed for analyzing surface degradation. The apparatus can include a sensor configured to acquire images of a surface; and a processing device configured to correlate the acquired images to a geo-coordinate, to extract at least one property of a surface abnormality identified in at least one of the acquired images, and to generate trend data based on changes over time in the at least one property of the surface abnormality identified in the images, which are correlated to a common geo-coordinate.

29 Claims, 5 Drawing Sheets

(56) References Cited

OTHER PUBLICATIONS

Christian Koch, et al. "Pothole Detection in Asphalt Pavement Images." *Journal of Advanced Engineering Informatics* (25)507-515. (2011). *Elsevier*.

"Schrankmonster: Technology-Ninja!" Web2PDF. Jan. 14, 2013.

Allan D. Behler, et al., "Rough Roads Ahead: Fix Them Now or Fix Them Later." AASHTO Trip 2009.

"'Street Bump': App Detects Potholes, Alerts Boston City Officials." pp. 1-2. Jul. 20, 2012. *Associated Press*.

OV5647 5 Megapixel Product Brief. Version 1-2. *OminVision*. Nov. 2010.

\* cited by examiner

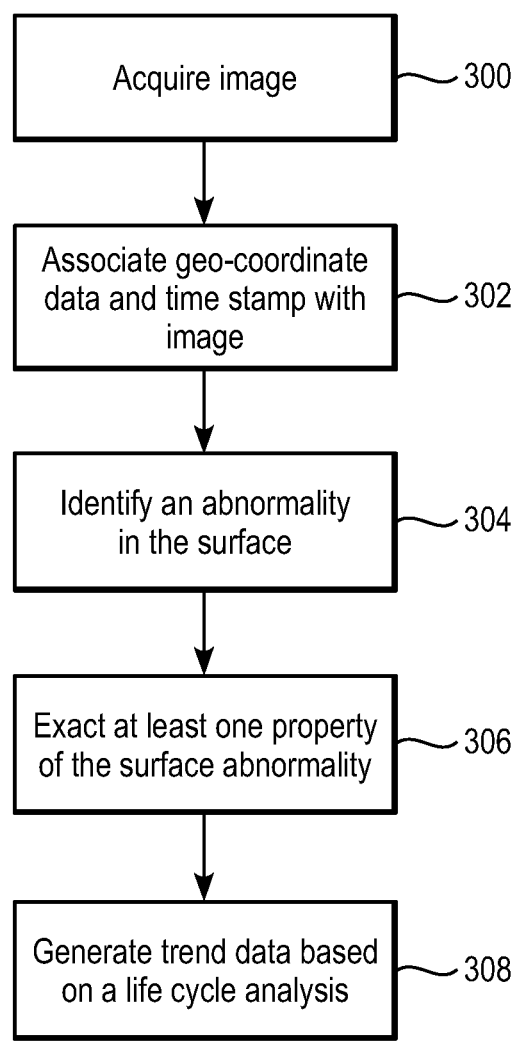

MOBILE POTHOLE DETECTION SYSTEM AND METHOD

FIELD

This disclosure relates to a surface imaging system such as a surface imaging system configured to detect abnormalities in the surface.

BACKGROUND

Road maintenance programs are associated with maintaining the quality and safety of road pavement and the pavement surface. Numerous systems and programs have been devised that survey roads and determine whether any portions or areas are distressed. These systems can use technologies such as lasers, cameras, and radar to perform surface analysis.

For example, in a known system, ground-penetrating radar is used with mapping technology to assess conditions that could affect the road pavement and the surface life of the road to assess remaining service life. The system uses a lap-top computer along with a GPS receiver to track road locations on a region map and gather data about a previous service life rating, historic data on a segment of road, and previous repairs to the road surface.

In another known system, an automatic road analyzer is used to collect information on surface roughness, rutting, and cracking. The data is fed to a processor that identifies targets for both pavement preservation and rehabilitation fixes.

In yet another known system, an automated distress survey is used to assess pavement conditions and calculate crack density in defining an appropriate preventive maintenance treatment. Various sections of pavement that represent all treatment types, stress levels, and traffic volume are monitored in an effort to visually assess effectiveness of the preservation strategy.

The implementation of these systems and programs can be labor and time intensive. Because of shrinking budgets and declining infrastructure, road maintenance departments can be faced with the challenge of performing maintenance with fewer people. The cost to maintain a road maintenance system or program also involves expense of servicing maintenance vehicles and equipment which can strain budgets and prevent a system from being used at its full capacity.

SUMMARY

An exemplary system for analyzing a surface subject to degradation is disclosed, the system comprising: a sensor configured to acquire at least one image of a surface; a first processing device configured to associate a time stamp and geo-coordinate data with each acquired image to identify when a surface abnormality is present in the at least one acquired image, and to select at least one of the acquired images which shows the surface abnormality; and a second processing device configured to extract at least one property of the surface abnormality identified in the at least one selected image, to store data representing the extracted property in a database, and to generate trend data of the surface by analyzing surface degradation over time based on the at least one property extracted from plural images correlated to a common geo-coordinate.

An exemplary apparatus for analyzing surface degradation is disclosed, the apparatus comprising: a sensor configured to acquire images of a surface; and a processing device configured to correlate the acquired images to a geo-coordinate, to extract at least one property of a surface abnormality identified in at least one of the acquired images, and to generate trend data based on changes over time in the at least one property of the surface abnormality identified in the images, which are correlated to a common geo-coordinate.

An exemplary method of identifying surface degradation is disclosed, the method comprising: acquiring images of a surface from a sensor; associating the acquired images with geo-coordinate data; processing the acquired images to identify an abnormality in the surface and extract at least one property of the surface abnormality; and generating trend data on a selected abnormality by analyzing changes over time in the at least one property extracted from images correlated to a common geo-coordinate.

An exemplary non-transitory computer readable medium is disclosed, the computer readable medium having programming code recorded thereon such that when placed in communicable contact with a processor, the processor executes a method of measuring surface degradation, which comprises: acquiring at least one image of a surface; associating the at least one acquired image with geo-coordinate data; processing the at least one acquired image to identify an abnormality in the surface and to extract at least one property of the surface abnormality identified in the at least one acquired image; and generating trend data on the surface abnormality by analyzing surface degradation over time based on the at least one property extracted from plural images correlated to a common geo-coordinate.

DESCRIPTION OF THE DRAWINGS

In the following, the disclosure will be described in greater detail by way of exemplary embodiments and with reference to the attached drawings, in which:

FIG. 3 illustrates a method of identifying surface degradation in accordance with an exemplary embodiment of the present disclosure.

DETAILED DESCRIPTION

Exemplary embodiments of the present disclosure are directed to a system that can provide automated field collection of images and that can continuously monitor a surface, such as a road surface, and analyze acquired data so that road characteristics such as deterioration or abnormalities in the surface can be repaired as they occur. An exemplary system disclosed herein can be compact, inexpensive, and can be mounted in or on a vehicle without complex or labor-intensive modifications to the vehicle.

An exemplary system described herein can reduce vehicle and manpower costs for municipalities by providing data driven preventative planning, thereby optimizing repair routes and schedules, and precision road condition reporting using existing service vehicles and routes. Material costs can also be reduced through the provision for detailed service breakdown analyses, a reduction in the time interval in acquiring a surface survey, and increased effectiveness of preventative maintenance. Exemplary embodiments of the present disclosure provide a system that can be inexpensively maintained and be used as a standalone system or integrated with existing surface and/or pavement management systems.

Figure 1:
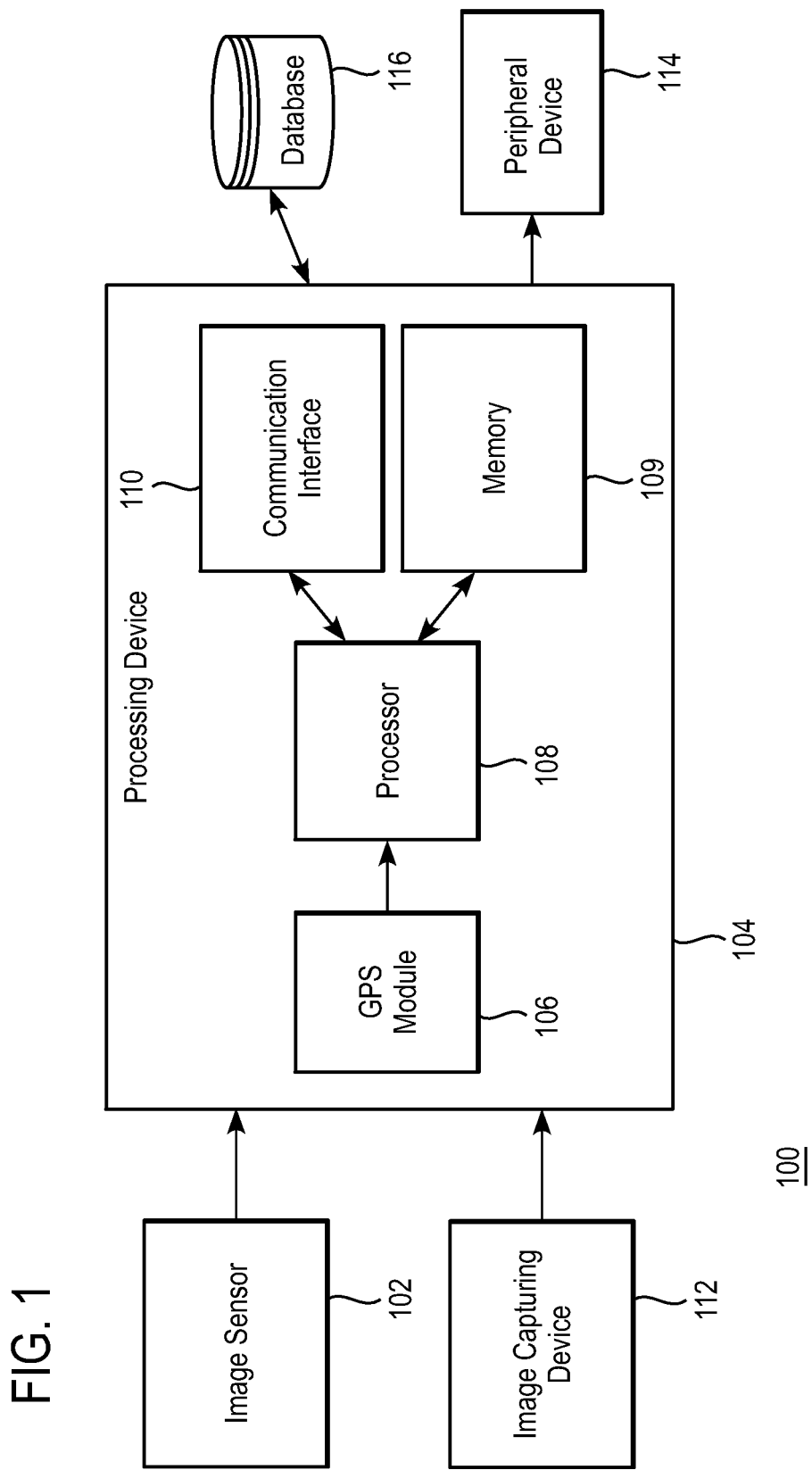
FIG. 1 illustrates a system for analyzing a surface in accordance with an exemplary embodiment of the present disclosure.

FIG. 1 illustrates a system for analyzing a surface in accordance with an exemplary embodiment of the present disclosure. As described in the context of the present disclosure, the surface can include a face or plane that is subject to wear or deterioration due to environmental conditions and/or use by vehicles. In the context of the present disclosure, the vehicle can be any mode of transportation with or without an engine and having one or more axles, such as a car, motorcycle, bicycle, truck or any other suitable transport mode that enables images of a surface to be captured at a desired location or over a desired distance. The surface can include materials such as concrete, asphalt, any combination thereof, or other materials suitable for forming a road surface as desired.

As shown in FIG. 1, the system 100 includes a sensor 102 configured to acquire at least one image of a surface. The image sensor 102 can include at least one of a camera or accelerometer. For example, in an exemplary embodiment the image sensor 102 can include a 5-megapixel camera with a ¼ inch lens and a frame rate of at least 720p/60 high definition HD video capture. The camera can provide 720p and 1080p HD video at 30 frames per second. The camera can also be configured to support both video and snapshot operations at a ¼ μm×¼ μm pixel size. In an exemplary embodiment, the image sensor 102 can include at least one accelerometer configured to measure acceleration due to vibrations caused when the vehicle on which the image sensor is encounters a surface abnormality.

The system 100 also includes a processing device 104 configured to associate a time stamp and geo-coordinate data with each acquired image to identify when a surface abnormality is present in the at least one acquired image, and to select at least one of the acquired images which shows the abnormality in the surface. A surface abnormality can be any designated characteristic of the surface subject to change over tie including but not limited to a crack, rut, pothole, buckle, cup, ridge, and/or or any other surface characteristic caused through wear or deterioration of the surface materials, or which results from any form of surface modification or treatment (e.g., application of paint or other desired or undesired coating).

The processing device 104 can be configured to be small and compact in size and can be mounted on or in the vehicle. In an exemplary embodiment, the processing device 104 can include a plurality of components, such as modules, circuits, and processors that are mounted on a printed circuit board (PCB). The processing device 104 can include a global positioning system (GPS) module 106 that connects to any number of satellites of a global positioning system (GPS) to provide location (e.g., geo-coordinate) and time information. The location and time information acquired from the GPS is associated with the acquired images. The processing device 104 can also include a processor 108 configured to extract at least one feature from the acquired images, determine whether the extracted features identify an abnormality in the surface, and select at least one of the acquired images based on the determination.

For example, in an exemplary embodiment the acquired images encompass a video in which the processor 108 analyzes each frame in the image to determine a likelihood that any of the frames include an abnormality. Those frames determined to contain an abnormality are selected. This level of image processing performed by the first processing device 104 can be determined by the size and speed of the processor and memory.

For example, in another exemplary embodiment, each frame in the set of images can be transformed to obtain a gray-scale image. Filters can be applied to the gray-scale images to reduce and/or remove noise. After noise is removed, the images can be further processed, for example, the entire image or portions thereof can be compared to template images to determine whether an abnormality exists. The images determined to contain an abnormality are selected and communicated to another processor or processing device for further analysis.

In yet another exemplary embodiment, the first processing device 104 can apply any of a number of image segmentation algorithms to the images. For example, a thresholding algorithm can be performed on each image to generate a binary image. The thresholding can include any of a histogram shape-method, clustering-based method, entropy-based method, object-attribute-based method, spatial method, local method, or any other suitable thresholding technique as desired. Using an exemplary histogram shape-method, a triangle algorithm can be applied to the images. The images can be filtered and a threshold established at a specified point on the histogram, which has a maximum distance to a line that intersects the histogram's origin and a point that designates the maximum intensity. The threshold is used to convert the image into a binary image, where abnormalities in the image can be identified. The processor 108 selects those images that contain abnormalities and stores the images in memory 109. The selected images can also be communicated to another processing device for further processing.

The processing device 104 can include a communication interface 110 that enables the images and data to be transmitted over wired or wireless media. For example, the communication interface 110 can be configured to transfer the selected images to at least one of an external processing device and peripheral device including a display, speaker, printer, or any other peripheral device as desired. The communication interface 110 can include at least one of a network communication unit having an Ethernet connection port and a Universal Serial Bus (USB) port, which enable connection and/or communication with the other processing devices or peripherals. In an exemplary embodiment, the processing device 104 can be implemented as a small compact device, such as Raspberry Pi®, or other similarly-sized processing device.

The processing device 104 can be configured to extract at least one property of the surface abnormality identified in the at least one selected image, to store data representing the extracted property in a database, and to generate trend data of the surface by analyzing surface degradation over time, based on the at least one property extracted from plural images correlated to a common geo-coordinate. The property of the surface abnormality can include any one or a combination of type, size or dimensions, location, time, or any other suitable descriptive property as desired. In an exemplary embodiment of the present disclosure the type of abnormality can include for example a crack, rut, pothole, buckle, cup, ridge, and/or or any other surface characteristic caused through wear or deterioration of the surface materials or through surface modification or treatment as already discussed. The size of the abnormality, for example, can include any combination of length, width, depth, radius, or any other suitable measurement characteristic as desired. In another exemplary embodiment, the location of the abnormality can be conveyed as geo-coordinates, street name, nearest street address, nearest cross streets, distance from landmark, mile marker, or any other suitable information used to designate the location of the abnormality as desired. The processing device 104 can be configured to identify the extracted features of the surface abnormality and determine the associated dimensions.

The communication interface 110 can enable the receipt of image data in the processing device 104 from an external image capturing device 112 over a network. For example, the image capturing device 112 can include a mobile telecommunications device, such as a cellular phone with a camera, a hand-held digital camera, or any other device configured to communicate data to the processing device 104 over a telecommunication network, such as a computer network, the Internet, a telephone network, or other suitable network. Upon receipt of images from a mobile telecommunications device, the processing device 104 extracts the image along with metadata, which indicates a time of image capture and geo-coordinate location at which the image was captured.

The processing device 104 scans the received images and correlates those images having the same geo-coordinate data into an image data set. The processing device 104 includes an integrated memory device 109 for storing the image data set. Once the image data set is established, the second processing device 104 can be configured to extract at least one property of the surface abnormality from the acquired images associated with the common geo-coordinate. The property extraction can involve pattern recognition techniques according to known image processing algorithms.

For example, in an exemplary embodiment, if image segmentation has not already been performed on the images, the images can be segmented using any of a number of image segmentation algorithms already discussed. Once the images have been segmented (e.g., converted into binary images) the identified abnormalities can be further analyzed based on a shape, position, and size of the abnormality as determined from features extracted from the binary images. These features can be determined, for example, based on a number of pixels, length of a major axis, position of a centroid, orientation angle. Further processing, such as thinning or filtering, can be performed on the image to determine shape and/or identify additional characteristics or properties of the abnormality.

The textures of surfaces within an image can be analyzed to determine whether an abnormality (e.g., pothole, cracks, cup, ridge, etc.) exists. For example, various areas of the image (e.g., image frame) can be compared with surrounding areas to determine the likelihood that an abnormality is shown in the image frame. If an abnormality is determined to be present, the processor 104 via the image processing algorithm can then determine the type of abnormality by comparing properties of the subject pixel region with templates stored in memory 109.

In another exemplary embodiment, the processing device 104 can process the images using a wavelet transform algorithm. Under this exemplary technique, the processing device 104 is configured to separate each image in the set of images into multiple levels. For example, in a first stage of the wavelet transform, the processing device 104 passes an image in parallel through two filters (e.g., high pass filter and low pass filter) such that two different versions of the image are generated. A second stage of the wavelet transform, can involve at least one of the first stage outputs being passed in parallel through two additional filters (high pass and low pass) such the original image is decomposed further. In an exemplary embodiment, the processing device 104 can include any number of wavelet transforms stages until the image is decomposed to a predetermined level. Once the final state of the wavelet transform is complete, the features at any of the various stages can be analyzed to identify and extract at least one property of the surface abnormality from the acquired image. Following extraction of the at least one property, the processing device 104 analyzes the property to determine the type of surface abnormality present at the common geo-coordinate. The images and identification data associated with the images are stored in a database 116.

The processing device 104 can be configured to generate trend data related to the surface abnormality identified at the common geo-coordinate based at least one of the extracted properties stored in the database 116 and characteristics of the surface. For example, when a predetermined number of images have been collected for a common geo-coordinate, and the images have been collected over a specified length of time (e.g., number of hours, days, months, years, etc.) the processing device 104 can use the extracted properties to analyze the changes in the surface abnormality over the time range specified by the set of images correlated to the common geo-coordinate. The characteristic conditions of the surface can include static characteristics, environmental characteristics, and dynamic characteristics which are considered along with the properties extracted from the images to forecast a life-cycle of surface abnormality.

In accordance with an exemplary embodiment of the current disclosure, the static characteristics can include the composition of materials in the surface (e.g., surface materials). Further, the environmental characteristics can specify the type of surface (e.g., a sidewalk, bike path, driveway, tarmac, city street, interstate, or any other surface as designated) and the terrain in which the surface is located (vegetation density, building or home density, hilly, flat, etc.). In addition, the dynamic characteristics that can be considered during the life-cycle computation can specify traffic volume, temperature (including average temperature), traffic type (single and multi-axle vehicles, pedestrians, bicycle, heavy machinery, or other type as specified), climate (e.g., rainy, humid, arid, etc.).

The processing device 104 can compute the forecast of the life-cycle to determine at least one of optimal materials and an optimal technique for use in repairing the surface abnormality. The life-cycle forecast can be computed based on any of a number of known forecasting methods including a quantitative, a time series, neural network, or other known techniques as desired. In an exemplary embodiment, the processing device 104 can be configured to compute the forecast based on a time-series method including any one of a moving average, weighted moving average, Kalman filtering, exponential smoothing, extrapolation, linear prediction, trend estimation, growth curve, or other suitable methods as desired.

The processing device 104 can be configured to compute the life cycle forecast automatically or based on a query of the database 116. For example, the processing device 104 can be connected to a peripheral device 114, such as a display, user interface, keyboard, mouse, printer, or other suitable device as desired. Through the peripheral device 114, a user could query the database 116 with respect to a specific geo-coordinate or area of geo-coordinates. A pothole at the geo-coordinate or a list of potholes within a specified proximity to the geo-coordinate can be identified and presented to the user through the peripheral device 114, for example, a display. The user can be prompted to select any number of the listed potholes so that a life-cycle forecast can be computed.

In an exemplary embodiment, the forecast can include the generation of a durability report, which is produced based on trending data focused on the composition of materials used in the original surface construction or a repair operation of the surface. In generating the durability report, the database 116 can access characteristic conditions of the surface (e.g., static, environmental, dynamic, etc.), which along with other properties and data associated with the pothole and repair, and execute an algorithm that uses the data to determine a repair life expectancy of the pothole at the specified geo-coordinate.

Once generated, the report can be output to a user through a suitable peripheral device 114 or can be communicated to another electronic device or peripheral device for output. In another exemplary embodiment, the peripheral device 114 can be configured to output a waveform or image representative of the extracted properties and/or surface abnormalities present in an acquired image.

According to exemplary embodiments of the present disclosure, the processing device 104 can include one or more processors mounted on the PCB. In another exemplary embodiment, the one or more processors can be connected remotely such that at least one processor is mounted on the PCB and the at least one other processor is external to the PCB. As a result, processing of the images can be performed in part by the at least one processor mounted on the PCB, and partly by the at least one processor external to the PCB.

Figure 2A:
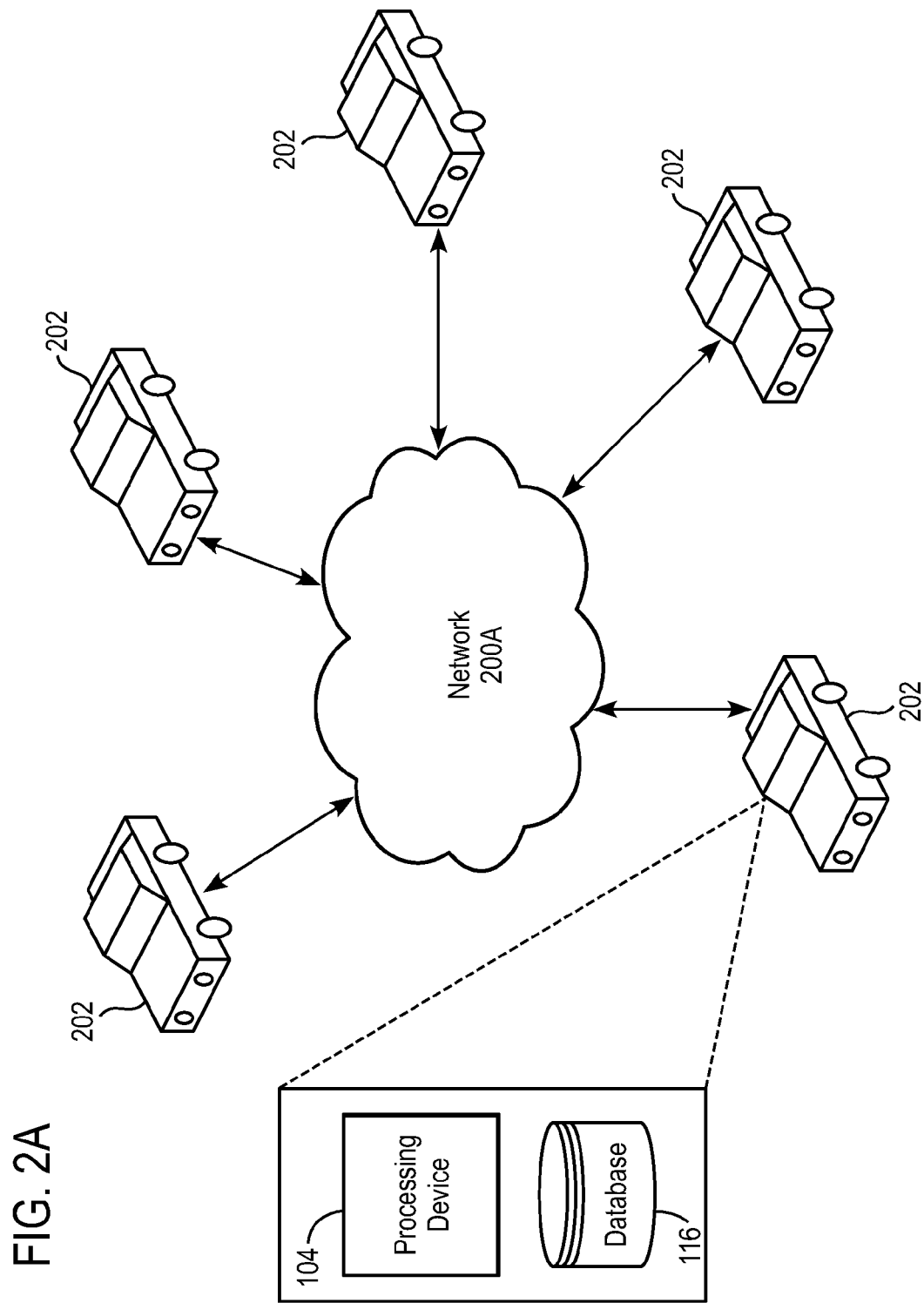
FIGS. 2A-2C illustrate various configurations of the system 100 in accordance with an exemplary embodiment of the present disclosure.
Figure 2B:
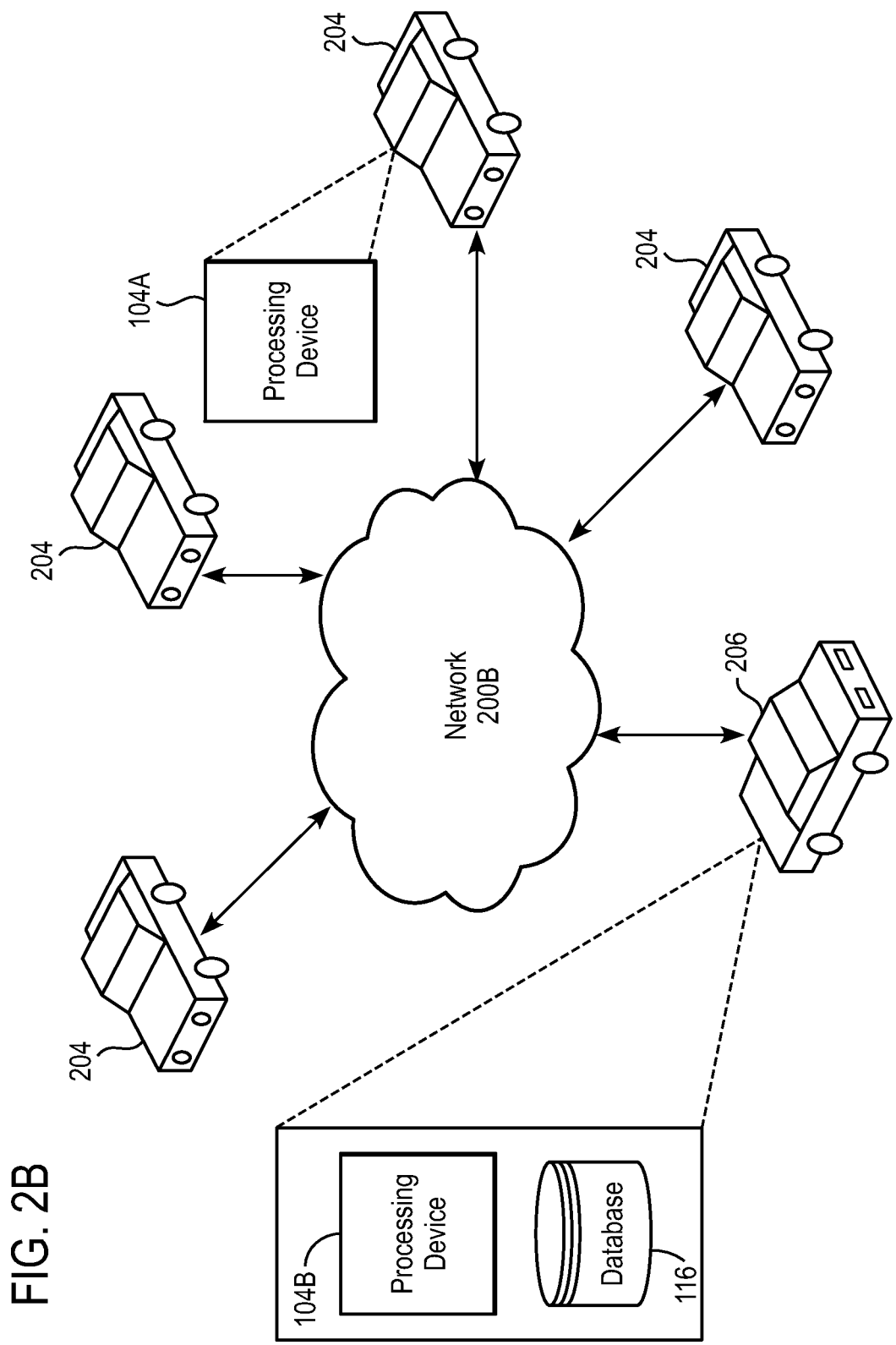
Figure 2C:
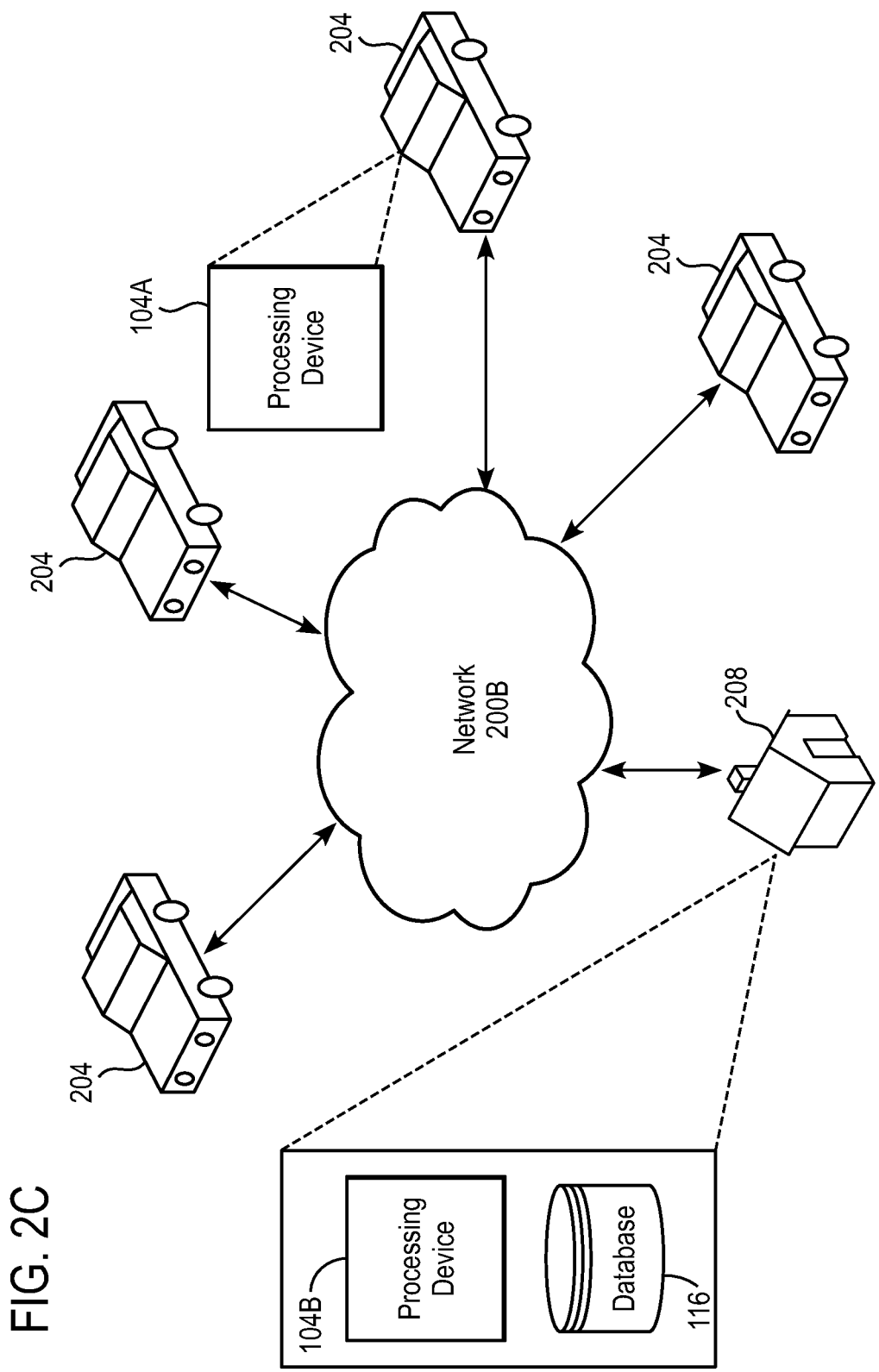

FIGS. 2A-2C illustrate various configurations of the system 100 in accordance with an exemplary embodiment of the present disclosure. As already discussed in accordance with exemplary embodiments of the present disclosure, the system 100 can be an integrated unit including at least the image sensor 102, the first processing device 104, the database 116.

As shown in FIG. 2A, the system 100 can be arranged in a network 200A that includes a plurality of vehicles 202 each having a system 100 mounted thereon. The network 200A can be configured as a distributed network such that each vehicle 202 functions as an autonomous processing node. Each node 202 in the network 200A can be configured to communicate acquired images and life cycle computations to every other node 202 in the network 200A such that all nodes the data stored at one node 202 is duplicated among all nodes in the network 200A. Because of this arrangement, a query of data and/or life cycle analysis can be performed at any vehicle 202 (e.g., node) in the network 200A.

In another exemplary embodiment as illustrated in FIG. 2B, the network 200B can be configured such that the image sensor 102 and a processing device 104A are mounted on a plurality of first vehicles 204 and another processing device 104B and database 116 are mounted on at least one second vehicle 206 (e.g., base or building). In this arrangement, any of the first vehicles 204 can communicate acquired images, processed images, and life cycle computations to the at least one second vehicle 206. In another exemplary embodiment, the processing device 104B of the at least one second vehicle 206 can be configured to process images received from the processing device 104A of the first vehicle 204 by performing any unexecuted steps of the image processing algorithm along with the life cycle analysis. The at least one second vehicle 206 stores all of the image and computational data in the database 116. In this manner, all queries can be performed by accessing the data stored at a central location.

FIG. 2C illustrates a variation of the exemplary network 200B in which the at least one second vehicle 206 is replaced with a base station or stationary location 208 for housing the processing device 104B and database 116.

FIG. 3 illustrates a method of identifying surface degradation in accordance with an exemplary embodiment of the present disclosure. The method can be executed by a system 100 discussed in relation to the features illustrated in FIG. 1. For example, the system for executing the method can include at least an image sensor 102, processing device 104, and a database 116 as discussed above.

As shown in step 300, images of a surface to be analyzed are acquired from an image sensor 102. The images can also be received from mobile communication devices 105 as already discussed. As already discussed, the image sensor 102 can be configured to capture video and static images of the surface. Moreover, the image sensor 102 can be coupled with an accelerometer 103, which acquires vibration data associated with the surface. Via the GPS module 106, the processing device 104 associates acquired images with a time stamp and geo-coordinate data (step 302). In step 304, the processing device 104 processes the acquired images to identify an abnormality in the surface. The processing device 104 also extracts at least one property of the surface abnormality (step 306). Next, the processing device 104, generates trend data in which a life cycle analysis is performed on a selected abnormality by analyzing changes over time in the at least one property extracted from images correlated to a common geo-coordinate (step 308).

As already discussed, the processing device 104 can include any of a number of processors. For example, the processing device 104 can have a first processing device 104a and a second processing device 104b, which can be mounted to the same vehicle or remotely from each other. In an exemplary embodiment in which the first and second processing devices 104a, 104b have a remote relationship, the first processing device 104a can format the selected images for transmission over a wireless network to the second processing device 104b. Upon receipt of the selected images, the second processing device 104b can process the images to identify the abnormality by extracting at least one property from the images, and generate trend data of the surface abnormality at a common geo-coordinate based on the at least one extracted property and existing surface characteristics. From the trend data, the processing device 104 can compute a life-cycle projection in which at least one of optimal (e.g., desired for a given or combination of static, environmental, or dynamic characteristics of the surface) materials and an optimal technique for use in repairing the surface abnormality are determined.

The one or more processors of the processing device 104 can be coupled to other processors or memory via a network. The processors can be configured through program code stored in a non-volatile memory device, such as Read-Only Memory (ROM), erasable programmable read-only memory (EPROM), or other suitable memory device or circuit as desired. In an exemplary embodiment, the program code can be recorded on a non-transitory computer readable medium, such as Magnetic Storage Media (e.g. hard disks, floppy discs, or magnetic tape), optical media (e.g., any type of compact disc (CD), or any type of digital video disc (DVD), or other compatible non-volatile memory device as desired) and downloaded to the processors for execution as desired.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A system for analyzing a surface subject to degradation over time, comprising:

a sensor configured to acquire at least one image of a surface;

a first processing device configured to associate a time stamp and geo-coordinate data with each acquired image to identify when a surface abnormality is present in the at least one acquired image, and to select at least one of the acquired images which shows the abnormality in the surface; and a second processing device configured to extract at least one property of the surface abnormality identified in the at least one selected image, to store data representing the extracted property in a database, and to generate trend data of the surface by analyzing surface degradation over time based on the at least one property extracted from plural images correlated to a common geo-coordinate, wherein the second processing device is configured to generate trend data based on at least characteristic conditions of the surface including static characteristics of the surface in combination with at least one of dynamic and environmental characteristics associated with the surface and forecast a life-cycle of the surface abnormality based on the characteristic conditions of the surface and the at least one property extracted from the plural images.

2. The system of claim 1, wherein the sensor includes at least one of a camera or accelerometer.

3. The system of claim 2, wherein a resolution of the camera is selected as a function of a processing speed of the processor.

4. The system of claim 1, wherein the first processing device includes:
   a GPS module configured to tag each acquired image with the time stamp and geo-coordinate data; and
   a processor configured to extract at least one feature from the acquired images, determine whether the extracted features identify an abnormality in the surface, and select at least one of the acquired images based on the determination; and
   a communication interface configured to transfer selected images to the second processing device.

5. The system of claim 4, wherein the communication interface includes at least one of a network card and a Universal Serial Bus (USB) port.

6. The system of claim 1, wherein the second processing device is configured to extract features from the acquired images using a wavelet transform.

7. The system of claim 6, wherein the second processing device is configured to identify the surface abnormality based on the extracted features.

8. The system of claim 7, wherein the second processing device is configured to determine dimensions of the surface abnormality.

9. The system of claim 1, wherein the second processing device comprises:
   a communication interface and is configured to receive image data from an image capturing device via the communication interface.

10. The system of claim 6, wherein the second processing device is configured to correlate at least two of the acquired images to the common geo-coordinate.

11. The system of claim 10, wherein the second processing device is configured to extract the at least one property of the surface abnormality from the acquired images of the common geo-coordinate using a wavelet transform.

12. The system of claim 11, wherein the second processing device is configured to identify the surface abnormality at the common geo-coordinate based on the at least one extracted property.

13. The system of claim 11, wherein the second processing device is configured to generate trend data of the surface abnormality at the common geo-coordinate based on the at least one extracted property.

14. The system of claim 11, wherein the second processing device is configured to determine at least one of optimal materials and an optimal technique for use in repairing the surface abnormality from the trend data.

15. The system of claim 4, wherein at least the GPS module, the processor, and the network interface are mounted in a housing.

16. The system of claim 15, wherein the housing is configured to be mounted on a vehicle.

17. An apparatus for analyzing surface degradation over time, comprising:
   a sensor configured to acquire images of a surface; and
   a processing device configured to correlate the acquired images to a geo-coordinate, to extract at least one property of a surface abnormality identified in at least one of the acquired images, and to generate trend data based on changes over time in the at least one property of the surface abnormality identified in the images, which are correlated to a common geo-coordinate,
   wherein the processing device generates trend data based on at least characteristic conditions of the surface including static characteristics of the surface in combination with at least one of dynamic and environmental characteristics associated with the surface and forecasts a life-cycle of the surface abnormality based on the characteristic conditions of the surface and the at least one property of the surface abnormality extracted from the at least one acquired image.

18. The apparatus of claim 17, comprising:
   a GPS module configured to tag each acquired image with a time stamp and geo-coordinate data; and
   a storage device configured to store the extracted data and the trend data.

19. The apparatus of claim 18, comprising:
   a network card configured to transfer at least one of the extracted data and the trend data to an external device.

20. A method of identifying surface degradation, comprising:
   acquiring images of a surface from a sensor;
   associating the acquired images with geo-coordinate data;
   processing the acquired images to identify an abnormality in the surface and extract at least one property of the surface abnormality;
   generating trend data on a selected abnormality by analyzing changes over time in the at least one property extracted from images correlated to a common geo-coordinate, wherein the trend data is generated based on characteristic conditions including static characteristics of the surface in combination with on at least one of dynamic and environmental characteristics of the surface; and
   forecasting a life-cycle of the surface abnormality based on the characteristic conditions and the at least one property of the surface abnormality extracted from the acquired images.

21. The method of claim 20, comprising:
   associating a time stamp with the images.

22. The method of claim 20, comprising:
   formatting the selected images for transmission over a wireless network.

23. The method of claim 22, comprising:
   acquiring the image data from the sensor.

24. The method of claim 20, comprising:
   determining at least one of optimal materials and an optimal technique for use in repairing the surface abnormality from the trend data.

25. The method of claim 20, comprising:
  determining at least one of optimal materials and an optimal technique for use in repairing the surface abnormality from the trend data.

26. A non-transitory computer readable medium having programming code recorded thereon such that when placed in communicable contact with a processor, the processor executes a method of measuring surface degradation over time comprising:
  acquiring at least one image of a surface;
  associating the at least one acquired image with geo-coordinate data;
  processing the at least one acquired image to identify an abnormality in the surface and to extract at least one property of the surface abnormality identified in the at least one acquired image using a wavelet transform; and
  generating trend data on the surface abnormality and forecasting a life-cycle of the surface abnormality by analyzing surface degradation over time based on the at least one property extracted from plural images correlated to a common geo-coordinate and characteristic conditions of the surface including static characteristics of the surface in combination with at least one of dynamic and environmental characteristics associated with the surface.

27. The system of claim 1, wherein the dynamic characteristics include at least one of traffic volume, temperature, traffic type, and climate.

28. The system of claim 1, wherein the environmental characteristics include at least one of surface type and type of terrain in which the surface is located.

29. The system of claim 1, wherein the static characteristics include a material composition of the surface.

* * * * *